United States Patent [19]

Reese

[11] Patent Number: 4,688,561

[45] Date of Patent: Aug. 25, 1987

[54] BONE HANDLING APPARATUS AND METHOD

[76] Inventor: H. William Reese, 3214 S. River, Tempe, Ariz. 85282

[21] Appl. No.: 776,772

[22] Filed: Sep. 17, 1985

[51] Int. Cl.⁴ .............................................. A61F 5/04
[52] U.S. Cl. ................................ 128/92 YF; 128/335
[58] Field of Search ........ 128/92 YY, 92 YF, 92 YD, 128/92 YE

[56] References Cited

U.S. PATENT DOCUMENTS

| | | | |
|---|---|---|---|
| 2,075,508 | 3/1937 | Davidson | 128/335 |
| 3,664,345 | 5/1972 | Dabbs et al. | 128/335 |
| 3,910,281 | 10/1975 | Kletschka et al. | 128/335 |
| 4,007,743 | 2/1977 | Blake | 128/335 |

Primary Examiner—John D. Yasko
Assistant Examiner—C. W. Shedd
Attorney, Agent, or Firm—Harry M. Weiss & Associates

[57] ABSTRACT

A bone handling apparatus and method incorporating thereto a flexible elongated member having a plurality of apertures for use as engagement means integral therethroughout the body of said flexible elongated member suitable for passing through an aperture through a bone for snugly engaging at least two broken or cracked portions of said bone is disclosed. A first end of said flexible elongated member has an integral locking means comprising a barb-type member protruding therefrom said first end. A second end, oppositely located from said first end, is suitable for accommodating a removable locking means comprising of at least a pair of female-type engagement connector member means. Alternatively, the elongated member may have a bottom portion suitable for accommodating a preferably rigid member for guiding said elongated member passing through the bone and an upper portion which may have a plurality of compartment-like sections or grooves for accommodating thereto a removable locking means comprising of at least a pair of female-type engagement connector member means.

10 Claims, 30 Drawing Figures

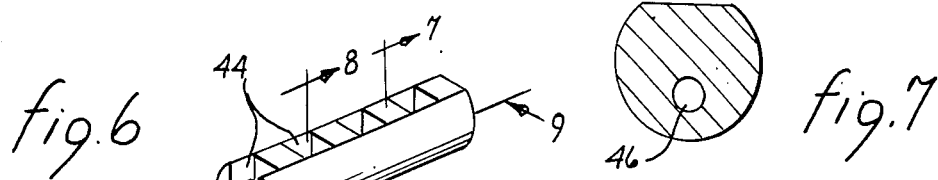

ns and Method

BONE HANDLING APPARATUS AND METHOD

BACKGROUND OF THE INVENTION

This invention relates generally to an apparatus and method for handling bones. More particularly, the invention relates to a preferably flexible elongated member having a plurality of female-type engagement means integral therethroughout the body of said flexible elongated member suitable for passing through an aperture through a bone for snugly engaging at least two broken portions of said bone in order to achieve an accelerated healing process. A first end of said flexible elongated member has an integral locking means while a second end, oppositely located from said first end, has removable locking means suitable for engaging the bone handling apparatus when in use.

Due to various abnormal events which cause significant stresses to be exerted on the human body, the human bones tend to absorb a considerable amount of these stresses which subsequently lead to the bones being cracked or broken. Consequently, due to numerous proximately adjacent nerves being detrimentally affected by the cracked or broken bones, a considerable amount of pain and suffering are experienced. Accordingly, the bone handling apparatus and method for the present invention, when used, will permit not only a rapid healing of the broken or cracked bone, but a more stable recuperation as well.

As most frequently experienced by elderly people, due to the susceptibility of slow deterioration which results in fragile and weakened bones, paid and suffering due to broken or cracked bones are realities which must be reckoned with.

Moreover, if a portion of a bone is removed or excised due to disease or abnormal growth, a means by which healthy portions are joined together to permit rapid and stable healing is by way of the bone handling apparatus and method of the present invention.

Accordingly, there is a dire need for an efficient, economical, simply constructed and easily installed handling apparatus and method for joining portions of a bone. Further, the bone handling apparatus and method should embody a simply constructed combination of inexpensive, easily accessible and rapidly manufactured parts, yet efficient to join portions of a bone or a plurality of bones together rapidly and effectively.

SUMMARY OF THE INVENTION

It is an object of the present invention to provide a handling apparatus and method for aiding in the healing process of bones and soft tissues atached thereto.

It is still another object of the present invention to provide a bone handling apparatus and method which generally comprises a combination of inexpensive and rapidly manufactured parts.

It is still another object of the present invention to provide a bone handling apparatus and method for easy insertion across a cracked or broken bone to aid in the rapid and stable healing process.

It is yet another object of the present invention to accomplish the above by a bone handling apparatus and method utilizing therefrom parts which will be durable in construction, long-lasting, economical and efficient when in use.

It is a more particular object of the present invention to provide a bone handling apparatus and method incorporating therein a flexible elongated member having a plurality of apertures for use as engagement means integral therethroughout the body of said flexible elongated member suitable for passing through an aperture through a bone for snugly engaging at least two broken or cracked portions of said bone.

It is another more particular object of the present invention to provide a first end of said flexible elongated member having an integral locking means comprising of a barb-type member protruding therefrom said first end suitable for accommodating a preferably rigid member for guiding said elongated member passing through the bone.

It is another more particular object of the present invention to provide a second end, oppositely located from said first end, suitable for accommodating a removable locking means comprising of at least a pair of female-type engagement connector member means.

It is a further more particular object of the present invention to alternatively provide an elongated member having a bottom portion suitable for accommodating a preferably rigid member for guiding said elongated member passing through the bone and an upper portion having a plurality of compartment-like sections for accommodating thereto a removable locking means comprising of at least a pair of female-type engagement connector member means.

It is a further more particular object of the present invention to alternatively provide an elongated member having a bottom portion suitable for accommodating a preferably rigid member for guiding said elongated member passing through the bone and an upper portion having a plurality of grooves for accommodating thereto a removable locking means comprising of at least a pair of engagement connector member means.

The foregoing and other objects, features and advantages of this invention will be apparent from the following, more particular description of the preferred embodiments of this invention as illustrated in the accompanying drawings.

BRIEF DESCRIPTION OF THE DRAWINGS

FIG. 2a is a perspective view of a first female-type engagement connector means of the present invention. FIG. 2b is a perspective view of a second female-type engagement connector means of the present invention. FIG. 2c is a side elevational view of the first female-type engagement connector means shown in FIG. 2a.

FIG. 6 is a perspective view of another embodiment of the present invention showing an elongated strip member suitable for accommodating a rigid elongated member for guiding said elongated strip member through the bone aperture.

FIG. 7 is a cross-sectional view taken in the direction 7—7 of FIG. 6 of said another embodiment of said elongated strip member of the present invention.

FIG. 8 is a cross-sectional view taken in the direction 8—8 of FIG. 6 of said another embodiment of said elongated strip member of the present invention.

FIG. 9 is a schematic diagram by which said another embodiment of the flexible elongated strip member is locked into said another embodiment of the first and second female-type engagement connector means.

FIG. 10 is an elevational view of another embodiment of a first female-type engagement connector means of the present invention.

FIG. 11 is an elevational view of another embodiment of a second female-type engagement connector means of the present invention.

FIG. 11a is a side elevational view of another embodiment of the second female-type engagement connector means of the present invention.

FIG. 12 is a side elevational view of another embodiment of the present invention showing an elongated strip member suitable for accommodating a rigid elongated member for guiding said elongated strip member through the bone aperture.

FIG. 13 is a top elevational view of said another embodiment of the present invention showing an elongated strip member suitable for accommodating a rigid elongated member for guiding said elongated strip member through the bone aperture.

FIG. 14 is a cross-sectional view taken in the direction 14—14 of FIG. 12 of said another embodiment of said elongated strip member of the present invention.

FIG. 15 is a cross-sectional view taken in the direction 15—15 of FIG. 12 of said another embodiment of said elongated strip member of the present invention.

FIG. 19b is a side elevational view of said first female-type engagement connection means shown in FIG. 19a.

FIG. 20b is a side elevational view of said second female-type engagement connector means shown in FIG. 20a.

DESCRIPTION OF THE PREFERRED EMBODIMENT

Figure 1A:
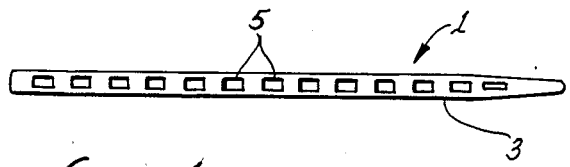
FIG. 1a is an elevational view of one embodiment of the present invention showing a flexible elongated strip member having a plurality of generally uniform slots or apertures passing therethrough.
Figure 1B:
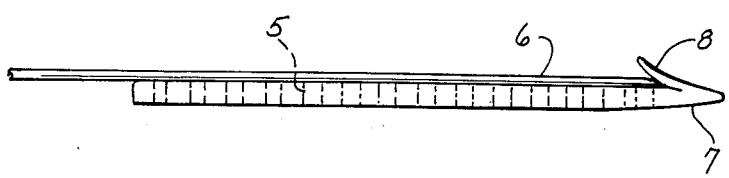
FIG. 1b is an elevational view of one embodiment of the present invention showing the flexible elongated strip member having an integral barb-type end portion suitable for accommodating a preferably rigid member for guiding said elongated member passing through the bone.

FIGS. 1a and 1b are elevational views of a bone handling apparatus, generally designated by reference number 1, having a flexible elongated strip member 3 with a plurality of slots or apertures 5 passing therethrough. The flexible elongated strip member 3 is preferably made of a non-absorbable, durable, long-lasting and economical material, such as nylon or absorbable material, if desired. As clearly shown in FIG. 1b, the flexible strip member 3 has a first end 7 having a barb-type member 8 integrally coupled thereto suitable for accommodating thereto a preferably rigid member 6 for guiding said elongated strip member 3 through a bone aperture (see FIGS. 4 and 5, infra.)

Figures 2A, 2B, 2C:
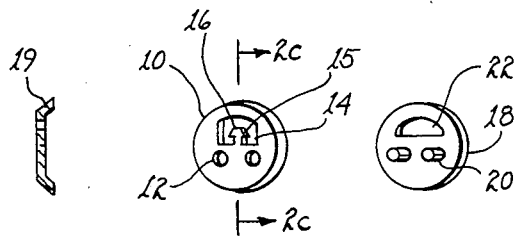

In FIG. 2a, a first female-type engagement connector means 10 is shown wherein at least two circularly-shaped apertures 12 pass therethrough preferably a center portion of the first female-type engagement connector means 10. At a portion of the first female-type engagement connector means 10, an approximately semi-circular shaped aperture 14 passed therethrough and accommodated thereto a tongue-type member 16, having a head member 15, protruding therefrom approximately the center portion of the first female-type engagement connector means 10. In FIG. 2b, a second female-type engagement connector means 18 is shown wherein at least two protruding member 20 may extend perpendicularly from a center portion of the second female-type engagement connector means 18. At another portion of the second female-type engagement connector means 18 is a preferably semi-circular aperture 22 passing therethrough. As shown in FIG. 2c, at least a pair of extending leg members 19 protrude therefrom said female-type engagement connector means 10. Alternatively, the connector means 18 may have teeth (not shown) protruding therefrom.

Figure 3A:
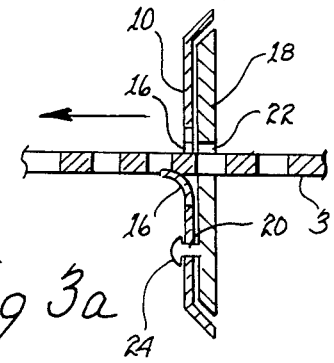
FIG. 3a is a schematic diagram by which the flexible elongated strip member is inserted, in the direction referred to by the arrow, into the first and second female-type engagement connector means.
Figure 3B:
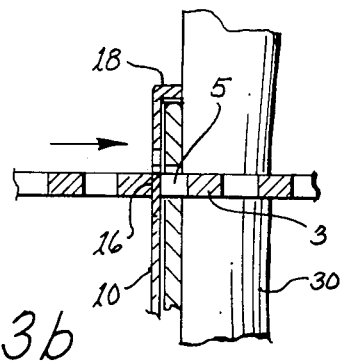
FIG. 3b is a schematic diagram by which the flexible elongated strip member is locked when longitudinally moved, in the direction referred to by the arrrow, into the first and second female-type engagement connector means.

The apertures 16, 12 are configured in such a manner as to allow the elongated strip member 3 to pass therethrough, as shown in FIG. 3a wherein the tongue-type member 16 is allowed to bend for accommodating said strip member 3. In order to rigidly lock the strip member 3, in the manner shown in FIG. 3a, a burr-type member 24 can be produced by melting the ends of the protruding members 20 to configurations suitable for sturdily locking together the first 10 and second 18 female-type engagement connector means. In order to appropriately lock the strip member 3 into the first 10 and second 18 female-type engagement connector means, the tongue-type member 16 is allowed to straighted and extend into at least one of the slots or apertures 5 of the strip member 3, as shown in FIG. 3b.

Figure 4:
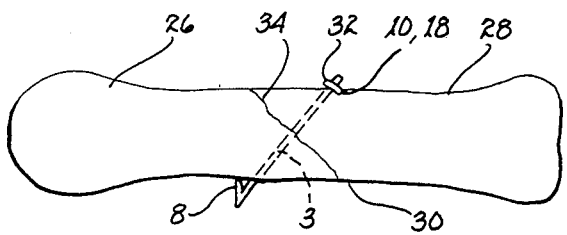
FIG. 4 is an elevational view of one manner in which the present invention is used for securing at least two sectional portions of a cracked or broken bone structure for purposes of advancing the healing process.

In FIG. 4, one manner in which the handling apparatus 1 is used for securing at least two sectional portions 26, 28 of a cracked or broken bone structure 30 is shown. Here, an aperture 32 is preferably drilled passing through the two section portions 26, 28 of the bone structure 30, the opening of which is suitable to accommodate therethrough the strip member 3. As shown in FIG. 4, the strip member 3 passes preferably perpendicular to the line of the crack 34 in order to maximize the effectivity of the handling apparatus 1 and to perhaps quicken and increase stability of the healing process. If desired, the handling apparatus 1 may be utilized in aiding in the healing process of relatively large cracted or broken bone structures, such as the femur, fibula or tibia of the leg or the humerus, ulna or radius of the arm or perhaps of relatively smaller bones, such as the metatarsals of the foot or metacarpals of the hand.

Figure 5:
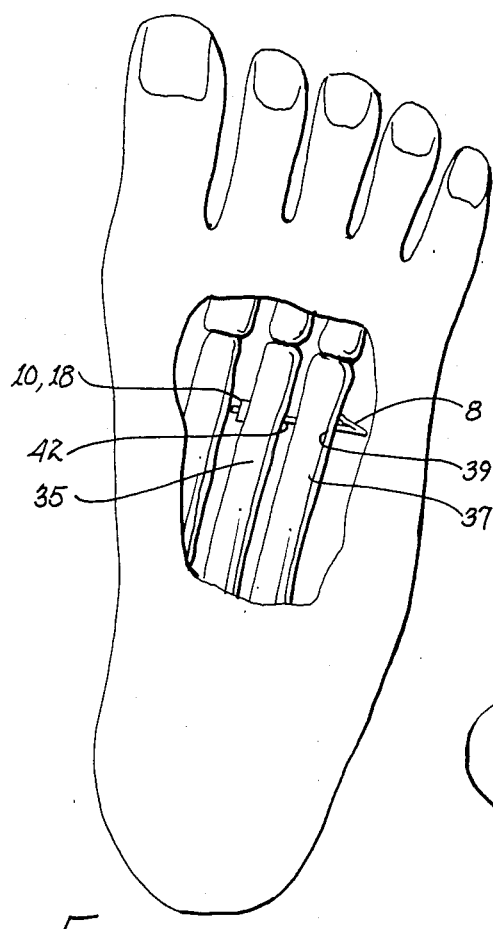
FIG. 5 is a sectional detail view of another manner in which the present invention is used for securing at least two adjacent bone structures (herein shown as metatarsals) for purposes of advancing the healing process.

As shown in FIG. 5, a sectional detail view of another manner in which the handling apparatus 1 is used for securing at least two adjacent bone structures 35, 37, herein illustrated as metatarsals; although they may be any proximately adjacent bone structures as, e.g., metacarpals of the hand. Here, apertures 39, 42 pass through the adjacent bone structures 35, 37 having preferably an equivalent line of axes.

In both manners of uses illustrated in FIGS. 5 and 6, the barb-type member 8 operates to impinge on one surface of the bone structure 30, 37 while the first 10 and second 18 female-type engagement connector means 10, 18 impinges on the oppositely located surface of the bone structure 30, 35, thereby allowing a more sturdy or efficient engagement and operation of the bone handling apparatus 1.

As illustrated in FIG. 6, an alternative embodiment of the present invention comprises a flexible elongated member having a plurality of compartment-like portions 44 at a preferably upper portion and aperture 46 passing therethrough longitudinally along a preferably bottom portion, as further illustrated in the cross-sectional views in FIGS. 7 and 8 along lines 7—7 and 8—8, respectively of FIG. 6. The aperture 46 accommodates thereto a rigid elongated member 48 for guidance therethrough the aperture 32, 39, 42 of the bone structure 30, 35, 37 as previously discussed. The manner in which an alternative first 49 and second 50 female-type engagement connector means are used to lock into at least one of the plurality of the compartment-like portios 44 is shown in FIG. 9. Here a protruding member 52 integral to the first female-type engagement connector means 49, see also FIG. 10, abouts an internally facing side 54 of at least one of the plurality of the compartment-like portions 4. As shown in FIG. 11, the aperture 56 passing therethrough the second female-type engagement connector means 50 is suitable for accommodating the elongated strip member having therein the rigid elongated member 48. An alternative embodiment of the second female-type engagement connector means 50 is shown in FIG. 11a wherein a side 54 has a plurality of teeth-like members 58 for abutting the bone structure 30, 35, 37, as previously discussed, tendon or soft tissues (not shown) adjacent to said bone structure 30, 35, 37. Alternatively, the teeth-like members 58 may have generally flat external ends (not shown), if desired, to increase thereby the contact surface of said teeth-like members 58 when in use.

Alternatively, the flexible elongated strip member may be configured as shown in FIGS. 13 to 14 wherein a plurality of grooves 60 are integrally incorporated thereto. As shown in FIG. 15, an aperture 62 passes therethrough longitudinally along the bottom portion of said alternative elongated strip member to allow a rigid elongated member 64 to pass therethrough as more clearly illustrated in FIGS. 12 and 13.

As shown in FIG. 14, a cross-sectional view taken along line 14—14 of FIG. 12 shows a groove 60 integral to said elongated strip member while in FIG. 14, a cross-sectional view taken along line 15—15 of FIG. 12 shows aperture 62 passing longitudinally along said elongated strip member.

Figure 16A:
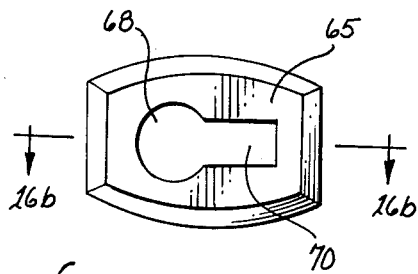
FIG. 16a is a top elevational view of another embodiment of a first female-type engagement connector means of the present invention.
Figure 17:
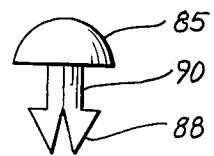
FIG. 17 is an elevational view of an embodiment of a plug-type engagement connector means for locking said first female-type engagement connector means of FIGS. 16a through 16c into said elongated strip member of FIGS. 12-13 of the present inventon.
Figure 16B:
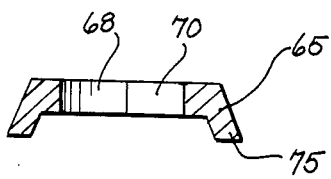
FIG. 16b is a side elevational view of a first female-type engagement connector means of the present invention.
Figure 18:
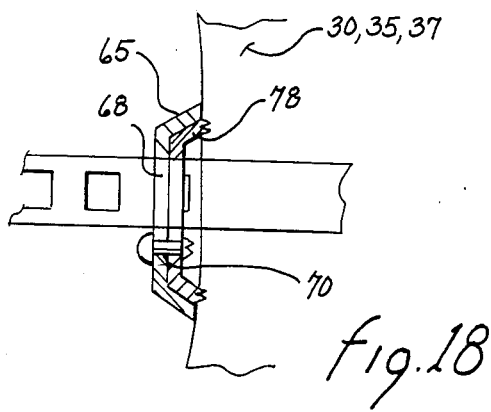
FIG. 18 is an elevational view of the manner in which the first female-type engagement connection means, the alternative second female-type engagement connection means, and the plug-type engagement connection means, as shown in FIGS. 16a, 16b and 17, respectively, are operably connected accommodating thereto the another embodiment of the elongated strip member shown in Figures 12-13.
Figure 16C:
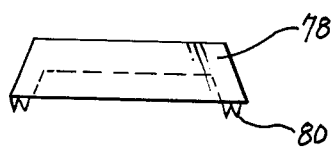
FIG. 16c is a side elevational view of another alternative embodiment of the second female-type engagement connector means of the present invention.

A first female-type engagement connector means 65 having a generally circular aperture 68 and an elongated aperture 70 communicating therethrough is provided as shown in FIGS. 16a and 16b having at least a pair of legs 75 preferably extending angularly therefrom. A second connector means 78 may have a plurality of teeth-like members 80 protruding therefrom the base of each of the legs 75. To allow the first female-type engagement connector means 65 and the second female-type engagement connector means 78 to be sturdily coupled to the elongated strip member shown in FIGS. 12-13 passing through the bone structure 30, 35, 37, a plug-type engagement connection means 85 having at least a pair of flexible leg members 88. The plug-type engagement connector means has a central portion 90 suitable for sliding into the elongated aperture 70 of the first female-type engagement connection means 65, as better illustrated in FIG. 18, thereby allowing engagement between the first 65 and second 78 female-type engagement connector means with the elongated strip member shown in FIGS. 12-13 passing through the bone structure 30, 35, 37.

Figure 19A:
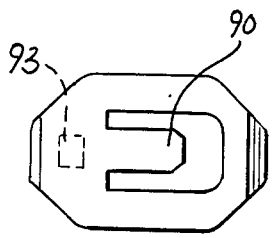
FIG. 19a is a top elevational view of another embodiment of the first female-type engagement connection means of the present invention.
Figure 20A:
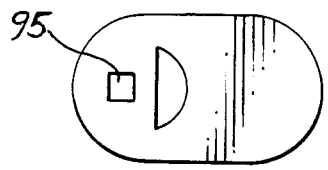
FIG. 20a is a top elevational view of another embodiment of the second female-type engagement connector means of the present invention.
Figure 20B:
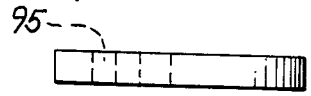
Figure 19B:
Figure 19C:
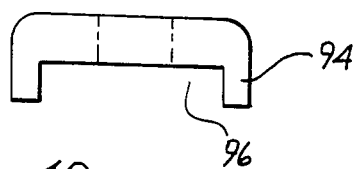
FIG. 19c is a side elevational view of the female-type engagement connection means shown in FIG. 19b.

As illustrated in FIGS. 19a–19c, another alternative embodiment of the first female-type engagement means are provided incorporating therein a protruding member 90 with an extending member 93 for being accommodated into an aperture 95 of another alternative embodiment of the second female-type engagement means. The first female-type engagement means may incorporate therein at least a pair of leg members 94 having a space therebetween to accommodate thereto said another alternative embodiment of the first female-type engagement means.

While the invention has been particularly shown and described in reference to preferred embodiments thereof, it will be understood by those skilled in the art that changes in form and details or various combinations thereof of the described features may be made without departing from the spirit and scope of the invention.

I claim:

1. An apparatus for fixing bones, comprising:
   flexible elongated strip means for passing through an aperture in a bone structure, wherein said strip means has a first end for protruding from a first end of said aperture and a second end for protruding from a second, opposed, end of said aperture and indentations therebetween for receiving a removable bone engagement means;
   deformable barb means having a first end integral with said first end of said strip means and a second end extending away from said strip means for engaging said bone at said first end of said aperture;
   pocket means extending substantially from said first to said second end of said strip means for removably receiving a rigid insertion tool for pushing said strip means through said aperture;
   removable bone engagement means having a central hole for sliding over said second end of said strip means and locking to said indentations in said strip means for making contact with said bone at said second end of said aperture for retaining said strip means firmly in said aperture, wherein said bone engagement means comprises at least two separable parts, a first part for bearing against said bone and a second part for bearing against said first part, wherein said central hole of said second part has a tang therein for engaging said indentations in said strip means.

2. The apparatus of claim 1 wherein said strip means is made of a material absorbable within a living body.

3. The apparatus of claim 1 wherein said strip means is selected from the group consisting of nylon and other non-absorbable material.

4. The apparatus of claim 1 wherein said first and second parts of said bone engagement means have at least one complementary hole and matching protrusion for locking the two parts together to prevent mutual rotation.

5. The apparatus of claim 1 wherein said second part of said bone engagement means substantially laterally surrounds said first part.

6. An apparatus for engaging a bone, comprising:
a flexible elongated plastic rod for passing through an aperture of said bone and having periodic indentations along its length;
a barb integrally formed on a first end of said flexible rod for locking onto a first side of said bone adjacent said aperture;
an engagement washer having a first side for pressing against said bone at a second end of said aperture, a second side opposite said first side, and an edge therebetween, wherein said engagement washer has a central through-hole for accepting said rod means;
rod locking means for pressing against said second side of said engagement washer and locking against said rod, wherein said rod locking means has a through-hole for accepting said rod and wherein a portion of said rod locking means deformably protrudes into said through-hole to engage said indentations in said rod; and
pin means extending between said engagement washer and said rod locking means for aligning and fixing said engagement washer and said rod locking means to prevent mutual rotation.

7. The apparatus of claim 6 wherein said rod locking means extends laterally outside and over said edge of said engagement washer.

8. The apparatus of claim 6 further comprising pocket means for receiving an insertion tool, wherein said pocket means extends substantially from said barb to a second end of said rod.

9. A method for repairing damaged bones, comprising:
providing an aperture of a predetermined length extending from a first to a second side of said bone;
providing a flexible rod having a deformable barb on a first end for engaging said first side of said bone, having a pocket at said first end for receiving an insertion tool, and having indentations for receiving a deformable tang;
providing a two part locking means for sliding over and engaging said rod and pressing against said second side of said bone, wherein said two part locking means comprises a first part for sliding over said rod and pressing against said bone and a second part having a deformable tang for sliding over and engaging said indentations in said rod, wherein said second part presses against said first part;
placing said insertion tool through said locking means into said pocket to form an assembly and inserting said assembly into said aperture barb end first;
while inserting said assembly compressing said barb to pass through said aperture until said barb protrudes from said second end of said aperture and springs back to its uncompressed shape;
sliding said locking means over a second end of said rod opposite said first end, leaving a length between said locking means and said barb exceeding said predetermined length; and
sliding said locking means toward said bone adjacent said second end of said aperture until said first part thereof engages said bone and said second part engages said first part, and then locking said deformable tang of said second part into one of said indentations in said rod.

10. The method of claim 9 wherein said step of providing said rod comprises providing a rod having a pocket extending longitudinally substantially from said first to said second end of said rod, and placing said insertion tool in said longitudinally extending pocket.

* * * * *